United States Patent [19]

Baird

[11] 4,251,231

[45] Feb. 17, 1981

[54] DIRECT PROCESS FOR THE PRODUCTION OF GASOHOL FROM FERMENTATION MIXTURES

[75] Inventor: James L. Baird, Winchester, Mass.

[73] Assignee: Artisan Industries Inc., Waltham, Mass.

[21] Appl. No.: 75,012

[22] Filed: Sep. 13, 1979

[51] Int. Cl.³ ............................................... C10L 1/02
[52] U.S. Cl. ......................................... 44/56; 44/53; 44/77
[58] Field of Search ......................... 44/53, 54, 56, 77; 203/18, 19

[56] References Cited

U.S. PATENT DOCUMENTS

| 1,937,786 | 12/1933 | Ricard et al. | 203/19 |
| 2,012,199 | 8/1935 | McElroy | 44/56 |
| 2,182,550 | 12/1939 | Christensen | 44/53 |
| 2,371,010 | 3/1945 | Wolfner | 44/56 |
| 2,591,672 | 4/1952 | Catterall | 203/18 |

*Primary Examiner*—Jacqueline V. Howard
*Attorney, Agent, or Firm*—Richard P. Crowley

[57] ABSTRACT

A process for the direct preparation of a gasohol from a low-content, water-alcohol solution of a fermentation broth, which solution contains ethanol or methanol, which process comprises mixing a low-volume alcohol solution, a solvent miscible in the alcohol and in the gasoline and a gasoline; discarding essentially alcohol-free water and recovering a gasohol composition of about 8% to 15% by volume of combined alcohol and solvent; removing water of saturation from the gasohol; and recovering substantially anhydrous gasohol.

22 Claims, No Drawings

DIRECT PROCESS FOR THE PRODUCTION OF GASOHOL FROM FERMENTATION MIXTURES

BACKGROUND OF THE INVENTION

Gasohol has been suggested widely as a substitute for gasoline and for combustion in internal-combustion engines. Typically, gasohol comprises a mixture of anhydrous alcohol and gasoline, with the alcohol present in an amount sufficient to be soluble in the gasoline. More particularly, gasohol is typically a mixture of approximately 6% to 12% by weight of alcohol, typically methanol or ethanol, and gasoline. The gasohol may contain other suitable additives, such as leaded or other antiknock additives, and, where applicable, surfactants, detergents, octane enhancers and promoters, such as tertiary methylbutyl ethyl ether and other additives, employed to enhance the combustion and performance of gasoline.

In the production of gasohol, substantially anhydrous alcohol is required for admixture with the gasoline, because of the very low water tolerance of the resulting gasohol mixture. This water tolerance often is in the range of approximately 0.2 to 0.5 weight percent of water. Higher amounts of water typically provide for unstable gasohol mixtures and lead to complete or partial separation of the water from the gasoline, the water being soluble in the methanol or ethanol, but insoluble in the gasoline, whether the gasoline is composed of highly aromatic or aliphatic components or a combination thereof.

Alcohols suitable for use in gasohol, particularly methanol and ethanol, are commonly made by the fermentation of various materials, such as sugar, corn and other grain-like or natural, fermentable materials. Fermentation broths or solutions produced often will contain up to approximately 12% alcohol in water; for example, 3% to 10%. The alcohol is separated from the water in the fermentation broth usually by a distillation process, which consumes a large amount of thermal energy. The production of anhydrous ethanol in particular requires an additional distillation step often utilizing an entraining or dehydrating solvent, such as benzene or other suitable liquid, to form a ternary solution. The addition of the benzene or other liquid is required, since ethanol and water form an azeotrope of approximately 95% alcohol and 5% water. The addition of benzene is required to permit the preparation of an anhydrous ethanol.

It would be most desirable to provide for the direct preparation of a gasohol from a fermentation broth and without the use of large amounts of thermal energy, as required in distillation, or the formation of azeotropes, with the need to add dehydrating solvents.

SUMMARY OF THE INVENTION

My invention is directed to a direct method for the production of gasohol and to the gasohol produced thereby. In particular, my invention relates to the direct production of substantially anhydrous gasohol suitable for combustion in internal-combustion engines from a fermentation-broth solution containing methanol or ethanol or admixtures thereof.

My invention involves the saving of considerable amounts of thermal energy by the direct extraction of the alcohol suitable for use in gasohol from a fermentation mixture by employing a gasoline as a solvent mixture in a liquid-liquid extraction process. However, the direct liquid-liquid mixing and extracting of methanol or ethanol, or mixtures thereof, from a fermentation broth, by the employment of a gasoline or gasoline-type product, are not directly possible, due to the substantially reduced solubility of the ethanol or methanol in the gasoline during the alcohol, water and gasoline liquid-liquid extraction process.

I have discovered, however, that gasohol may be prepared directly from fermentation broths or low-volume alcohol-water solutions employing gasoline as a solvent in a liquid-liquid mixing and extracting process, when the gasoline composition or the water-alcohol solution contains a small, but effective, amount of a solvent, which increases the solubility of the alcohol of the fermentation broth in the gasoline composition, therefore making feasible the savings of distillation energy or direct extraction of methanol or ethanol from a fermentation broth.

I have discovered that a suitable gasoline composition, for use in direct extraction of ethanol or methanol from a fermentation broth, comprises a gasoline, such as a naphtha, straight-run-type, unblended organic gasoline which may contain a small, but effective, amount of an alcohol solvent or an alcohol-misiclbe liquid therein, such as, for example, an alcohol like a $C_3$–$C_6$ alcohol; for example, a butanol, amyl alcohol, hexanol or combinations thereof, which are soluble in the gasoline. Typically, the amount of the solvent to be employed in the gasoline ranges from about 0.1% to 5% of the gasoline; for example, 0.5% to 3% of the gasoline by weight.

The solvent, such as the alcohol, may be added directly to a low alcohol-water solution or to the gasoline or to the ethanol to be extracted from the broth. The solvent may include, besides an alcohol, such other liquid organic combustion materials miscible with the ethanol or methanol, such as low-molecular-weight, volatile ethers, esters and ketones, but preferably and suitably is a lower, easily combustible, $C_3$–$C_6$ alcohol. Where an alcohol is employed, the butyl or amyl or other alcohols may be extracted from a fermentation broth employing the gasoline, and then the solvent alcohol contained in the gasoline composition then is employed in direct extraction of the methanol or ethanol from a suitable fermentation broth. In effect, my process provides in substance for shifting the plait points and shifting the operating line of a ternary-phase diagram composed of alcohol-water-gasoline, to provide gasohol with water therein. If desired, rather than using a miscible solvent, this shift may be accomplished by increasing the ionic strength of the water and reducing the solubility of the water through the use of additives, such as water-soluble salts like sodium chloride.

Thus, my process comprises the direct preparation of a substantially anhydrous gasohol; that is, gasoline containing methanol or ethanol or combinations thereof, with perhaps slight traces of other alcohols, from a fermentation broth containing the alcohols, and which process comprises, firstly, mixing and extracting the alcohol from the fermentation broth by employing, in a liquid-liquid extraction process, a gasoline composition which contains a solvent, which solvent increases the solubility of the methanol or ethanol in the gasoline composition, or preferably the additive alcohol is introduced with the weak ethanol of the broth, thereby permitting the direct extraction of the ethanol or methanol from the fermentation broth or mixture by the gasoline composition. Thereafter, a substantially anhydrous gasohol may be produced by removing whatever water of saturation occurs in the resulting extracted alcohol-gasoline composition product.

Removal of the water of saturation may be accomplished in a number of ways, such as the use of water adsorbents or absorbents, but preferably is accomplished by reducing the temperature of the extracted alcohol-gasoline product utilizing typical heat-exchange equipment to reduce the temperature to the level desired; for example, to below about $-10°$ F., such as below $-30°$ F. or $-40°$ F., thereby substantially reducing the water of saturation in the mixture and then decanting or otherwise removing the water of saturation from the gasohol and recovering a substantially anhydrous gasohol.

My process, therefore, avoids the formation of azeotropes and the use of large amounts of thermal energy and distillation steps and simplifies the number of steps involved and permits direct preparation of a substantially anhydrous gasohol directly from an alcohol-containing fermentation broth.

My process will be described for the purposes of illustration only in its preferred embodiment; however, it is recognized that various changes and modifications may be made to the process by those persons skilled in the art, all fully within the scope and purpose of my invention.

DESCRIPTION OF THE EMBODIMENTS

EXAMPLE

A gasohol composition is prepared comprising a weak ethanol-water solution (about 10% by volume alcohol) derived from a fermentation broth and from about up to 30%; for example, 15% to 25%, by volume of amyl alcohol, based on the ethanol content of the solution, as the alcohol-gasoline-miscible solution. The solution is then employed in a liquid-liquid extraction column and system (for example, employing sieve trays) as the heavy phase and then is intimately mixed in one or more stages in the column with an unleaded, blended, high-octane-type neptha gasoline as the light phase. In the liquid-liquid extraction process, the resultant mixtures are separated into their respective phases, with essentially ethanol-free water discarded and a gasohol containing approximately 8% to 15% by volume of combined alcohols in the gasoline. The gasohol so produced is further processed to reduce water of saturation therein to a lower acceptable level, such as by reducing the temperature of the gasohol in a heat exchanger. The choice of the additive used, such as amyl alcohol or other additives, depends on the ability to shift the plait point and the slope of the equilibrium tie lines to make the most favorable separation, and the additive may vary, depending on the type and composition of the gasoline used.

What I claim is:

1. A process for the direct preparation of gasohol from a low-content alcohol-containing solution from a fermentation broth, which process comprises:
   (a) mixing in a liquid-liquid extraction process a fermentation broth containing a methanol- or ethanol-water solution, the broth containing up to about 12% by volume of the methanol or ethanol, a gasoline composition and a small amount of up to about 30%, based on the alcohol content of the water-alcohol solution, of a solvent for the methanol or ethanol and miscible in the gasoline;
   (b) removing from the extraction process an essentially alcohol-free water;
   (c) removing a gasohol composition containing water of saturation, which composition contains from up to about 15% by volume of combined alcohol;
   (d) removing at least some of the water of saturation from the gasohol composition; and
   (e) recovering a substantially anhydrous gasohol.

2. The process of claim 1 wherein the solvent comprises from about 0.5% to 3% by weight of the gasoline of a $C_3$ to $C_6$ aliphatic alcohol.

3. The process of claim 2 wherein the organic alcohol is selected from the group consisting of isopropyl alcohol, butyl alcohol, amyl alcohol, hexanol and combinations thereof.

4. The process of claim 1 wherein the water of saturation is removed by employing water adsorbents.

5. The process of claim 1 wherein the water of saturation is removed by chilling the gasohol composition to a low temperature to reduce the solubility of the water of saturation and, thereafter, removing the water of saturation.

6. The process of claim 5 wherein the water of saturation is removed by decanting the water of saturation from the chilled gasohol composition.

7. The process of claim 5 which includes chilling the gasohol composition containing the water of saturation to a temperature of less than about $-30°$ F. and, thereafter, decanting the insoluble water of saturation.

8. The process of claim 1 wherein the gasoline composition comprises an unblended, naphtha-type, straight-run gasoline composition.

9. The process of claim 1 wherein the anhydrous gasohol comprises from about 85% to 93% by weight gasoline and 7% to 15% by weight of combined alcohol.

10. The process of claim 1 which includes the step of extracting butanol or amyl alcohol from a butyl or amyl-alcohol-containing fermentation broth employing gasoline and, thereafter, employing the butyl or amyl-alcohol-gasoline-extracted solution to extract the methanol or ethanol from the water-alcohol solution.

11. The substantially anhydrous gasohol produced by the process of claim 1.

12. A process for the direct preparation of substantially anhydrous gasohol suitable for use in an internal-combustion engine from a fermentation broth containing methanol or ethanol, which process comprises:
   (a) extracting in a liquid-liquid extraction process, from a methanol- or ethanol-containing fermentation broth, a methanol or ethanol from the broth employing as a solvent extractant an unblended, naphtha, straight-run gasoline composition in the presence of from about 0.1% to 5% by weight of a $C_3$ to $C_6$ alcohol to increase the solubility of the methanol or ethanol in the gasoline composition;
   (b) recovering a gasohol composition which comprises from about 85% to 93% gasoline and from about 7% to 15% of combined alcohol and contains water of saturation;
   (c) reducing the temperature of the extracted gasohol composition to approximately $-10°$ F. or below to render insoluble in such solution at least part of the water of saturation present therein; and
   (d) removing the water of saturation to provide a substantially anhydrous gasohol.

13. The substantially anhydrous gasohol produced by the process of claim 12.

14. The process of claim 1 which includes admixing the alcohol solvent with the alcohol-containing fermentation broth prior to mixing the fermentation broth with the gasoline composition.

15. The process of claim 1 which includes mixing the fermentation broth, the solvent and the gasoline composition in a liquid-liquid extraction column, wherein the fermentation broth is introduced as the heavy phase and the gasoline composition is introduced as the light phase, and wherein the solvent is in either phase.

16. A process for the direct preparation of substantially anhydrous gasohol from a fermentation broth containing ethanol or methanol, which process comprises:
   (a) introducing the aqueous fermentation broth, containing the ethanol or methanol as the heavy phase, in a liquid-liquid extraction column;
   (b) introducing a gasoline composition, into which gasoline composition it is desired to introduce alcohol to form a gasohol as the light phase in the liquid-liquid extraction column;
   (c) introducing into the light- or heavy-phase composition a solvent for the ethanol or methanol, and which solvent is also miscible in the gasoline composition;
   (d) admixing the broth, gasoline composition and solvent in a series of stages in the extraction column;
   (e) withdrawing from the extraction column a gasohol composition which comprises the gasoline composition, the solvent, the ethanol or methanol of the fermentation broth and water of saturation;
   (f) withdrawing from the extraction column an essentially methanol- or ethanol-free, aqueous, fermentation broth;
   (g) removing at least some of the water of saturation from the gasohol composition; and
   (h) recovering a substantially anhydrous gasohol.

17. The process of claim 16 wherein the solvent comprises a $C_3$ to $C_6$, volatile, low-molecular-weight alcohol.

18. The process of claim 17 wherein the anhydrous gasohol comprises from about 8% to 15% by volume of combined alcohol.

19. The process of claim 16 which includes reducing the temperature of the gasohol composition to $-10°$ F. or lower, to reduce the solubility of the water of saturation, and recanting from the low-temperature gasohol composition the separated water of saturation.

20. The process of claim 16 wherein the solvent comprises from about 0.1% to 5.0% by weight of the gasoline composition.

21. The process of claim 16 wherein the liquid-liquid extraction column contains a plurality of sieve plates.

22. The anhydrous gasohol produced by the process of claim 16.

* * * * *